(12) United States Patent
Brodbeck et al.

(10) Patent No.: US 11,426,187 B2
(45) Date of Patent: Aug. 30, 2022

(54) LAPAROSCOPIC FORCEPS INSTRUMENT

(71) Applicant: Erbe Elektromedizin GmbH, Tuebingen (DE)

(72) Inventors: Achim Brodbeck, Metzingen (DE); Matthias Voigtlaender, Gomaringen (DE); Bernhard Nold, Tuebingen (DE); Tim Closs, Berg (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 225 days.

(21) Appl. No.: 16/434,352

(22) Filed: Jun. 7, 2019

(65) Prior Publication Data

US 2019/0374240 A1 Dec. 12, 2019

(30) Foreign Application Priority Data

Jun. 8, 2018 (EP) ..................................... 18176834

(51) Int. Cl.
*A61B 17/29* (2006.01)
*A61B 18/14* (2006.01)

(52) U.S. Cl.
CPC .......... *A61B 17/29* (2013.01); *A61B 18/1442* (2013.01); *A61B 18/14* (2013.01);
(Continued)

(58) Field of Classification Search
CPC ............ A61B 17/29; A61B 2017/2901; A61B 2017/2939; A61B 2017/2948;
(Continued)

(56) References Cited

U.S. PATENT DOCUMENTS 1,754,806 A * 4/1930 Stevenson .............. A61B 17/24
606/174
4,721,116 A * 1/1988 Schintgen .............. A61B 10/02
600/564
(Continued)

FOREIGN PATENT DOCUMENTS

CN 103327922 A 9/2013
CN 105055020 A 11/2015
(Continued)

OTHER PUBLICATIONS

European Search Report dated Nov. 11, 2018, in corresponding European Application No. 18176834.2 (6 pgs.).
(Continued)

*Primary Examiner* — Dianne Dornbusch
(74) *Attorney, Agent, or Firm* — Fitch, Even, Tabin & Flannery LLP

(57) ABSTRACT

The forceps instrument includes a central pull-push member formed by transmission and actuating elements. The central push-pull member opens and closes the branches, and also acts as a tissue abutment that is variable based on the degree of closure of the branches. The variable tissue abutment may be configured as a slider element and is adjustable proportionally to the opening angle of the branches. When grasped, the vessels are brought proximally. The tissue abutment acts as a spacer between the hinge region and the grasped material. While the branches are being closed, the vessel is held stationary and compressed. During compression, expansion of the vessel occurs axially in distal and proximal directions. Due to the receding of the variable tissue abutment during the closing operation, room is created for the grasped material to escape. Tissue accumulations can thus be restricted and overstressing of the tissue can be counteracted.

7 Claims, 5 Drawing Sheets

(52) U.S. Cl.
CPC ............... *A61B 2017/2901* (2013.01); *A61B 2017/2939* (2013.01)

(58) Field of Classification Search
CPC . A61B 18/1442; A61B 18/1482; A61B 18/14; A61B 2017/2926; A61B 2017/2927; A61B 2017/2929; A61B 2017/293; A61B 2017/2931; A61B 2017/2932; A61B 2017/2933; A61B 2017/2934; A61B 2017/2936; A61B 2017/2938; A61B 2017/2947; A61B 18/1445; A61B 18/1447
See application file for complete search history.

(56) References Cited

U.S. PATENT DOCUMENTS

| | | | | |
|---|---|---|---|---|
| 5,373,854 | A * | 12/1994 | Kolozsi | A61B 10/06 600/562 |
| 5,496,317 | A | 3/1996 | Goble et al. | |
| 5,582,617 | A * | 12/1996 | Klieman | A61B 17/29 606/170 |
| 5,820,630 | A * | 10/1998 | Lind | A61B 10/06 606/208 |
| 6,063,103 | A * | 5/2000 | Hashiguchi | A61B 17/29 606/205 |
| 6,309,404 | B1 * | 10/2001 | Krzyzanowski | A61B 10/06 606/205 |
| 6,358,268 | B1 * | 3/2002 | Hunt | A61B 17/29 606/206 |
| 7,473,253 | B2 * | 1/2009 | Dycus | A61B 18/1445 606/51 |
| 7,887,535 | B2 * | 2/2011 | Lands | A61B 18/1445 606/51 |
| 8,409,200 | B2 * | 4/2013 | Holcomb | A61B 18/1445 606/51 |
| 9,055,961 | B2 | 6/2015 | Manzo et al. | |
| 9,655,672 | B2 | 5/2017 | Artale et al. | |
| 9,737,357 | B2 | 8/2017 | Dycus et al. | |
| 10,130,410 | B2 * | 11/2018 | Strobl | A61B 17/3205 |
| 2002/0058961 | A1 * | 5/2002 | Aguilar | A61M 29/02 606/198 |
| 2003/0120307 | A1 * | 6/2003 | Abergel | A61F 2/0095 606/207 |
| 2005/0033359 | A1 * | 2/2005 | Dycus | A61B 17/0057 606/213 |
| 2006/0217697 | A1 * | 9/2006 | Lau | A61B 18/085 606/29 |
| 2009/0018535 | A1 * | 1/2009 | Schechter | A61B 18/1445 606/33 |
| 2009/0062792 | A1 * | 3/2009 | Vakharia | A61B 18/1492 606/45 |
| 2009/0259248 | A1 * | 10/2009 | Ganter | A61B 17/29 606/205 |
| 2010/0179545 | A1 | 7/2010 | Twomey et al. | |
| 2015/0105821 | A1 * | 4/2015 | Ward | A61B 17/295 606/206 |
| 2016/0157923 | A1 | 6/2016 | Ding | |
| 2016/0199082 | A1 * | 7/2016 | Batchelor | A61B 17/2804 606/52 |
| 2016/0302844 | A1 * | 10/2016 | Strobl | A61B 17/3201 |
| 2016/0367311 | A1 * | 12/2016 | Gerrans | A61B 1/05 |
| 2018/0078268 | A1 | 3/2018 | Messerly et al. | |
| 2018/0132926 | A1 | 5/2018 | Asher et al. | |
| 2019/0053818 | A1 * | 2/2019 | Nelson | A61B 17/295 |

FOREIGN PATENT DOCUMENTS

| | | |
|---|---|---|
| JP | 2013165991 A | 8/2013 |
| RU | 53884 U1 | 10/2006 |
| WO | 2018/039412 A1 | 3/2018 |

OTHER PUBLICATIONS

Chinese First Office Action dated Feb. 22, 2022, in corresponding Chinese Application No. 201910492549.X, with English translation (18 pages).

Indian Office Action dated Mar. 31, 2022, in corresponding Indian Application No. 201914022493 (5 pages).

Russian Office Action dated Apr. 12, 2022, in corresponding Russian Application No. 2019116916/14(032337), with machine English translation (14 pages).

* cited by examiner

LAPAROSCOPIC FORCEPS INSTRUMENT

RELATED APPLICATION(S)

This application claims the benefit of European Patent Application No. 18176834.2, filed Jun. 8, 2018, the contents of which are incorporated herein by reference as if fully rewritten herein.

TECHNICAL FIELD

The invention relates to a forceps instrument, in particular to a forceps instrument for tissue fusion, in particular an instrument with reduced crushing tendency.

BACKGROUND

Forceps-like instruments used for pinching off, i.e., temporarily closing tissues, in particular however for permanently closing vessels by grasping, compressing, and coagulating the vessels by the application of an electrical current have been known—in principle—from prior art. Typically, such instruments comprise two branches, of which at least one is supported on the other so as to be movable relative to each other. A pivoting motion of the branch results in a relatively large change of distance on the distal ends of the branches, while only a small distance chance exists near the hinge. Therefore, a vessel grasped between the branches is compressed along the branch with varying strength. In the vicinity of the hinge it is possible that there is a tendency for crushing, so that a vessel is crushed or otherwise mechanically damaged due to excess pressure before said vessel is properly sealed, as a result of which a proper closure of the vessel can no longer be ensured.

Regarding this, publication US 2016/0157923 A1 describes an instrument designed for open surgery, said instrument having the form of a tissue fusion forceps with two branches that can be moved relative to each other and with a knife with which a sealed vessel can be severed. In order to avoid an uneven compression of the vessel, a tissue abutment is provided in the vicinity of the hinge, said abutment preventing the tissue from coming too close to the hinge.

The use of such a tissue abutment indeed prevents the advance of the tissue to the hinge, in which case, however, tissue crushing can still not be precluded.

Considering this, it the object of the invention to provide an improved forceps instrument.

SUMMARY

This object is achieved with the medical forceps instrument as described herein.

The forceps instrument according to the invention comprises two branches, at least one of them being movable so as to be pivotable in order to be able to move the branches toward each other and away from each other, i.e., be able to open and close the forceps instrument. Different types of biological material, in particular hollow vessels, that are to be temporarily or permanently closed can be grasped. Such vessels are grasped and compressed between the two branches. In doing so, the movable tissue abutment provided on the instrument in accordance with the invention initially prevents—with the forceps open, i.e., branches away from each other—the grasped vessel or other biological tissue from being able to move too close to the hinge of the forceps instrument.

The tissue abutment is arranged in a movable manner so that it, when the forceps instrument is being closed, may make available room for the tissue that is displaced by the branches. Preferably, in doing so, the tissue abutment is supported or guided in such a manner that its tissue abutment surface will be moved or be displaced in the direction toward the hinge when the branches are being closed.

The movement of the tissue abutment may be a guided movement that is coupled with the movement of the at least one pivotably movable branch. However, it is also possible to move the tissue abutment independent of a movement of the branches. To do so, the tissue abutment may be held and locked in a first position, for example, with the branches open, in which case the detent can be released by actuating a separate unlocking means or as a result of a movement of the branches during the closing movement. After releasing the detent, the tissue abutment may be freely movable or movable against a spring force, so that it can be moved by and yield to the displaced tissue. However, also the tissue abutment itself may be configured as a spring.

In a preferred embodiment of the forceps instrument both branches are supported so as to be movable toward each other and away from each other. In this manner it is possible in a simple manner to achieve a large opening angle of the forceps instrument, so that large tissue volumina and large-volume vessels can be grasped. In conjunction with this feature, the movably supported tissue abutment provides a good protection of grasped tissue against crushing. In particular, in the case of instruments in which both branches are supported so as to be pivotable about the same hinge axis, a crushing or constriction tendency of the grasped tissue or of vessels in the hinge region is drastically reduced. Consequently, the risk of a mechanical destruction of tissue is minimized or completely prevented. If the forceps element is a clamp for only the temporary closure of vessels, for example, a tissue damage is prevented. If the forceps instrument is an instrument for the permanent closure of a vessel, for example due to tissue fusion by coagulation, a reduction of the sealing strength or even the failure of the seal due to the prevention of crushing the tissue in the region close to the hinge, is prevented or at least the tendency to do so is minimized. Likewise, an inadvertent severing of the vessel is prevented.

With the invention, a sufficient distance between the grasped tissue and the hinge of the forceps instrument is ensured. This sufficient distance is different for different sizes of grasped tissue and for different vessel diameters. Due to a movement of the tissue abutment as a function of the opening angle of the tool, the safety distance for the grasped amount of tissue or the size of the grasped vessel between the tissue and the hinge is safely guaranteed.

With the invention, it is possible to reduce or prevent crushing zones on the biological tissue in the region close to the hinge. By minimizing the risk of pinching tissue in the hinge region, the function of the forceps instrument becomes safer and improved overall. Likewise, any tissue damage due to high pressing forces that could otherwise occur in the region close to the hinge are prevented and optionally reliably precluded.

The tissue abutment may be movably supported in diverse ways. In a preferred embodiment, it is configured as a slider element, and is supported so as to be translationally or, in particular, linearly movable. However, it is also possible to alternatively provide a tissue abutment that is support so as to be pivotally movable.

The tissue abutment may be configured as a slider element that has a plane, simply curved or doubly curved tissue abutment surface that represents, e.g., a blunt distal end of the slider element. In conjunction with this, a blunt surface is understood to mean any surface that is flat or rounded and does not have, or be delimited by, any sharp corners or edges that cut into the tissue. In particular, the tissue abutment surface may be an elongated surface having a cylindrical curvature in the center region and be additionally rounded in the two lateral end areas. The tissue abutment surface is then composed of a simply curved surface in the center and two doubly curved surfaces at the ends. The tissue abutment surface may be an elongated surface essentially parallel to the hinge axis that is formed on an end piece of the slider element. Preferably, the width to be measured parallel to the hinge axis is smaller, or at most approximately as great as, the width of a branch to be measured in the same direction, in particular the tissue abutment surface of the branch.

The tissue abutment is connected in a driven manner to at least one movably supported branch. For connection it is possible to use a transmission arrangement effective between the tissue abutment and the movable branch or branches. In particular, the tissue abutment may be connected to an actuating arrangement that is disposed to actuate the branches, in particular close said branches. The tissue abutment may be part of the actuating arrangement and, for example, be configured as a slider element with an extension projecting beyond the hinge in distal direction. Likewise, the transmission connection between the branches and the tissue abutment is preferably configured in such a manner that the tissue abutment moves in the direction toward the hinge, when the branch performs a closing movement and, in doing so, clears additional space for the tissue that is deformed during the closing operation and also protruding in the direction of the hinge.

If the forceps instrument is intended for a permanent vessel closure, the tissue abutment surfaces of both branches are preferably configured as electrodes and can be connected to an appropriate electrical source, in particular an RF generator. As a result of this, the tissue grasped between the branches can be heated and coagulated by the current flow. Vessels that are grasped between the branches and compressed can be fused. The electrodes may be connected to the power source via a switch to be actuated by the user, so that the coagulation takes place only as needed and under the control of the user.

It is possible to provide, on the forceps instrument, cutting devices in particular in the form of a mechanically cutting knife or in the form of a voltage-energized minimally movable or immovable electrically cutting knife, said devices severing grasped and coagulated tissue in the sealing region. In the case of such instruments, the tissue abutment prevents mechanical damage to the vessel to be closed and thus prevents an impairment of the seal.

BRIEF DESCRIPTION OF THE DRAWINGS

Additional details of advantageous embodiments of the invention are the subject matter of the drawings, the description or of the claims. The drawings show exemplary embodiments of the invention. They show in FIG. 1 a perspective schematic diagram of a forceps instrument according to the invention for laparoscopic use, FIG. 2 a side view of the forceps tool provided on the distal end of the instrument according to FIG. 1, FIG. 3 a perspective view of the forceps tool according to FIG. 2, FIG. 4 a side view of the forceps tool according to FIGS. 2 and 3, with semi-closed branches, FIG. 5 a perspective view of the forceps tool according to FIG. 4, FIG. 6 a side view of the forceps tool according to FIGS. 2 to 5, in closed position, FIG. 7 a perspective view of the forceps tool according to FIG. 6, FIG. 8 a side view of the branches, the slider element and the associate actuating arrangement of the forceps instrument according to FIGS. 1 to 7, FIG. 9 a perspective representation of an embodiment of a slider element of the forceps instrument according to the invention, FIG. 10 a perspective representation of another embodiment of the slider element of the forceps instrument according to the invention, FIG. 11 a side view of a modified embodiment of a forceps tool with the tissue abutment in opened position, and FIG. 12 a side view of the forceps instrument according to FIG. 11, in partially opened position.

DETAILED DESCRIPTION

Figure 1:
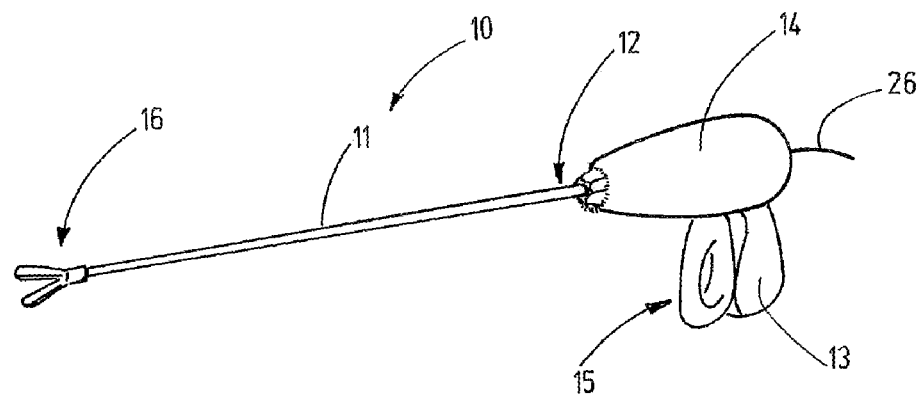

FIG. 1 shows a forceps instrument 10 that is set up for laparoscopic use. It is intended to illustrate the invention that can be implemented equally in instruments for open surgical use and also in instruments for endoscopic use.

The forceps instrument 10 according to FIG. 1 has an elongated stiff shaft 11 whose proximal end 12 is held by a housing 14 that is provided with a handle 13. In the vicinity of the handle 13, there is provided an actuating element 15 having, for example, the form of a pivoting lever.

Figure 2:
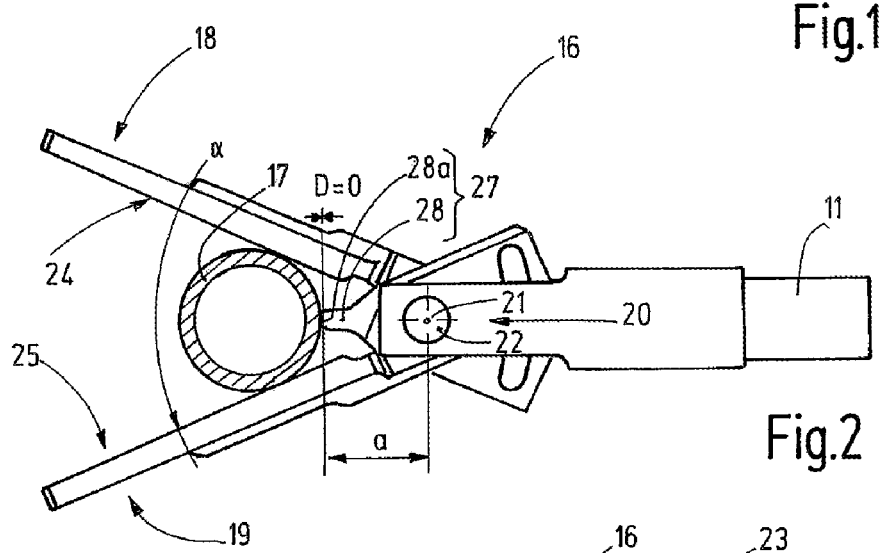
Figure 3:
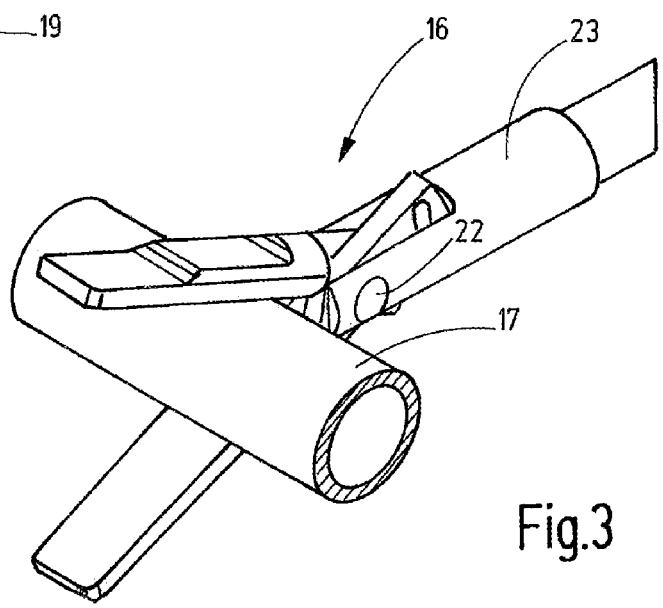

A forceps-like tool 16 is held on the distal end of the shaft 11, the design and function of said tool being clearer from FIGS. 2 and 3, and is disposed for grasping and/or clamping tissue, in particular biological vessels such as, for example the vessel 17 shown by FIGS. 2 and 3. The actuating element 15 is disposed for opening and closing the tool, said actuating element being in driven connection with the tool to accomplish this.

The tool 16 comprises two branches 18, 19, at least one or, as illustrated by FIGS. 2 and 3, both being supported in a pivotable manner A hinge 20 that defines a hinge axis 21, which is oriented transversely with respect to the shaft 11 and about which the two branches 18, 19 are pivotably supported, acts as a support. To do so, a hinge pin 22 is mounted in a forked hinge bearing 23 on both sides, in which case the branches 18, 19 are seated in the central region on said hinge bearing.

Each of the branches 18, 19 has flat one-dimensionally or also two-dimensionally or three-dimensionally profiled tissue support surfaces 24, 25, between which the vessel 17 or other biological tissue is to be grasped. The tissue support surfaces 24, 25 may be configured as planar, simply curved or doubly curved, convoluted, toothed surfaces and as electrodes that are insulated from each other, said electrodes being connected—via appropriate electrical conductors and a cable 26 (FIG. 1)—to a not specifically illustrated supply generator. The generator and the electrodes are disposed to pass electrical power through biological material grasped and compressed between the tissue support surfaces 24, 25 and to thus heat said material in order to achieve a desired surgical effect.

As the tissue abutment 27, the tool 16 comprises a slider element 28 whose rounded distal end defines a tissue abutment surface 28a. For supplemental illustration, reference is made to FIG. 10, in which the slider element 28 with its rounded tissue abutment surface 28 is shown in a separate embodiment. In doing so, said slider element is configured as a distal extension of a transmission element 29 that has a slotted hole cutout 30. The extension has a width b1 that corresponds to the width of the transmission element 29, for example, and that is less than the width of the support surface 24, 25 to be measured in the same direction parallel to the hinge axis 21.

Figure 8:
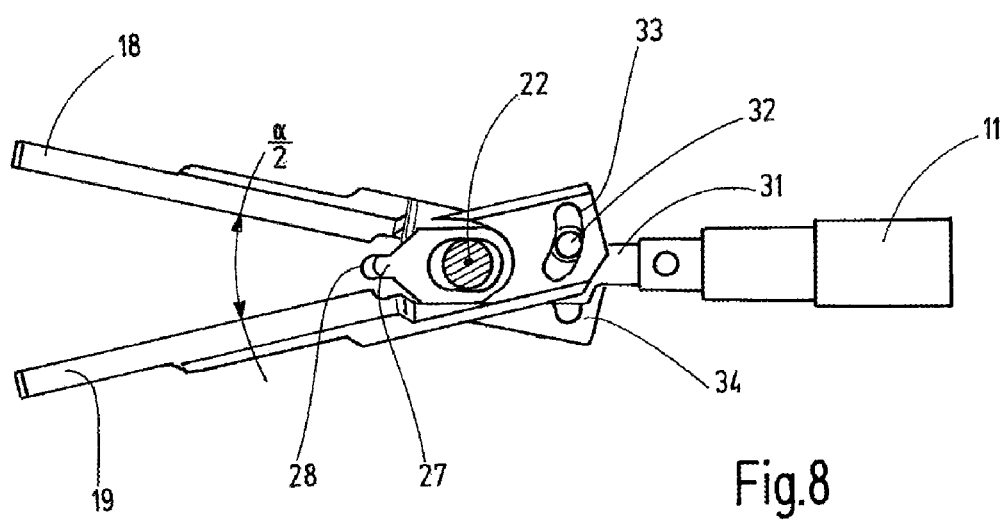

When assembled, the hinge pin 22, as shown by FIG. 8, extends through this slotted hole cutout 30. The oval slotted hole cutout 30 has a length—viewed in shaft longitudinal direction—that, together with the hinge pin 22, defines an axial longitudinal play that is at least as great as the desired axial path of the slider element 28. In the vertical direction to be measured transversely to the hinge pin 11 as well as transversely to the shaft longitudinal direction, the transmission element 29, however, is essentially seated without play on the hinge pin 22.

Adjoining the transmission element 29 in proximal direction, there is an actuating element 31 that extends through the shaft 11 or that is connected to a pulling element extending through the shaft 11. In the housing 14, this pulling element or the actuating element 31 itself is connected to an actuating mechanism in order to convert a pivoting motion of the actuating element 15 toward the handle 13 into a proximally directed motion of the transmission element 29.

The transmission element 29 comprises at least one follower pin 32 extending in a direction transversely away from the otherwise plate-shaped transmission element 29, said follower pin 32 being disposed for moving the branch 19. This branch has a bearing opening through which extends the hinge pin 22 with minimal play. As a result of this, the branch 19 is supported so as to be pivotable on the hinge pin 22. In the part of the branch 19—extending in proximal direction viewed from the hinge pin 22—there is formed a curved slotted hole 33 that, together with the follower pin 32, forms a connecting link guide as is illustrated by FIG. 8, in particular.

Figure 9:
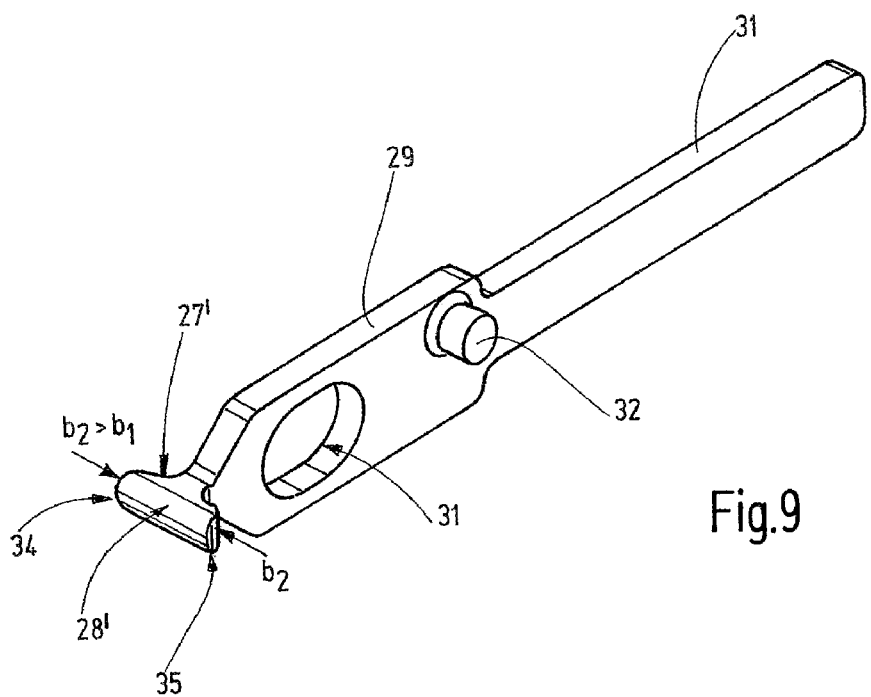
Figure 10:
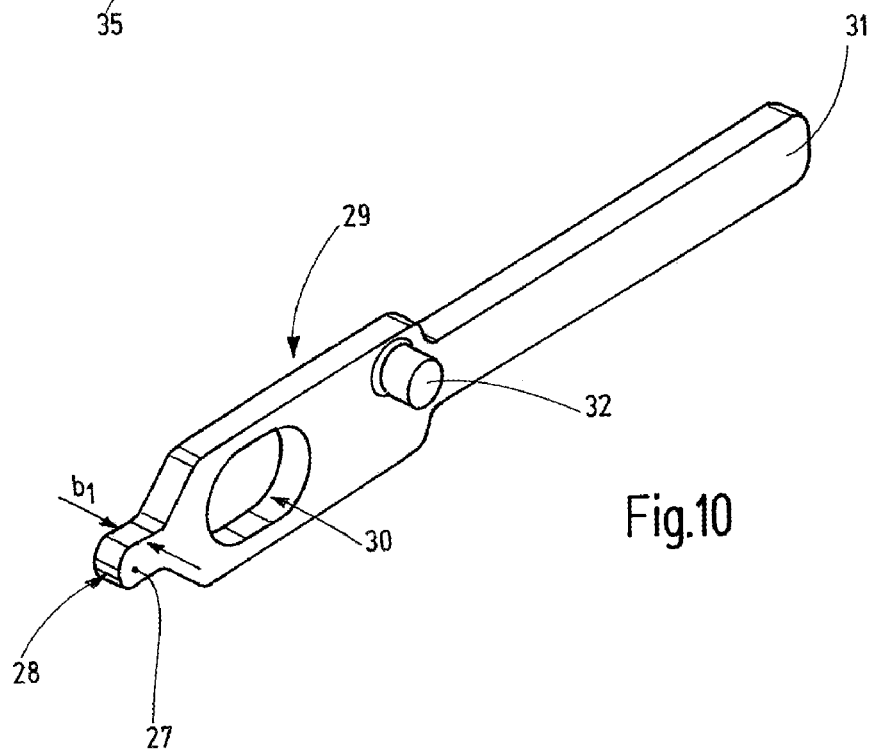

If both branches 18, 19 can be pivotally moved, the transmission element 29 has, on its opposite side, a flat such a follower pin that is arranged, however, on the side of the plate-shaped part of the transmission element 29 facing away from the viewer in FIGS. 9 and 10. This follower pin that cannot be seen in FIGS. 9 and 10 is also assigned a curved slotted hole 34 that is arranged in the proximal end of the branch 18 and forms a connecting link guide with the respective follower pin.

The variation of the radii of the slotted holes 33, 34 is defined in such a manner that a pulling movement of the actuating element 32 in proximal direction results in a closing of the branches 18, 19, i.e., in a movement toward each other.

As is shown by FIG. 9, the slider element 28 may also have a width b2 that is greater than the width of the transmission element 29. In this case, the slider element 28 forms a hammer head that projects on both sides symmetrically beyond the plate-shaped section of the transmission element 29. Preferably, the width b2 that is to be measured transversely with respect to the longitudinal direction of the shaft 11 and parallel to the hinge axis 21, is not greater than the width of the branches 18, 19. Like the tissue abutment surface 28a, the tissue abutment surface 28' is rounded and free of sharp edges. In particular, the tissue abutment surface 28a' is rounded relative to an axis located parallel to the hinge axis 21 (for example cylindrically), as well as also rounded on the face-side ends 34, 35.

The forceps instrument 10 described so far works as follows:

The forceps instrument 10 is positioned with its tool 16 on a patient in the vicinity of the vessel 17 to be grasped. To do so, for example, the shaft 11 may be pushed through a small cut, for example in the abdominal wall, into the abdominal cavity until the tool 16 grasps the biological tissue at a desired site, i.e., the vessel 12 is picked up. In doing so, the stiff shaft 11 is so stable that, by manipulating the housing 14 with the handle 13, the tool 16 can be moved back and forth as well as laterally.

When the vessel 17 has been grasped in accordance with FIGS. 2 and 3, it abuts against the tissue support surfaces 24, 25 and, at the same time, against the tissue abutment surface 28a. Because of this, it is held at a distance a from the hinge axis 21. The distance D of the tissue from the abutment surface 28a is zero, for example.

If now the forceps instrument is closed in that the actuating element 31 is moved in shaft longitudinal direction in proximal direction, for example by appropriate pivoting of the actuating element 15, the slider element 28 is moved in proximal direction at the same time. Regarding this, reference is made to FIGS. 4 and 5. As a result of the movement of the slider element 28 in proximal direction, the distance between the hinge axis 21 and the tissue abutment surface 28a decreases. The resultant distance b is smaller than the distance a explained in conjunction with FIGS. 2 and 3, while the instrument is fully opened.

Figure 4:
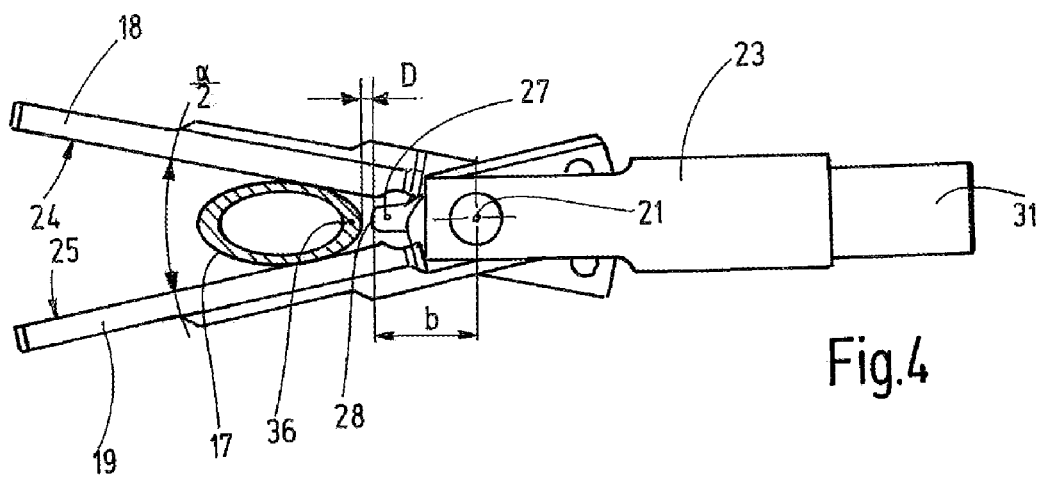
Figure 5:
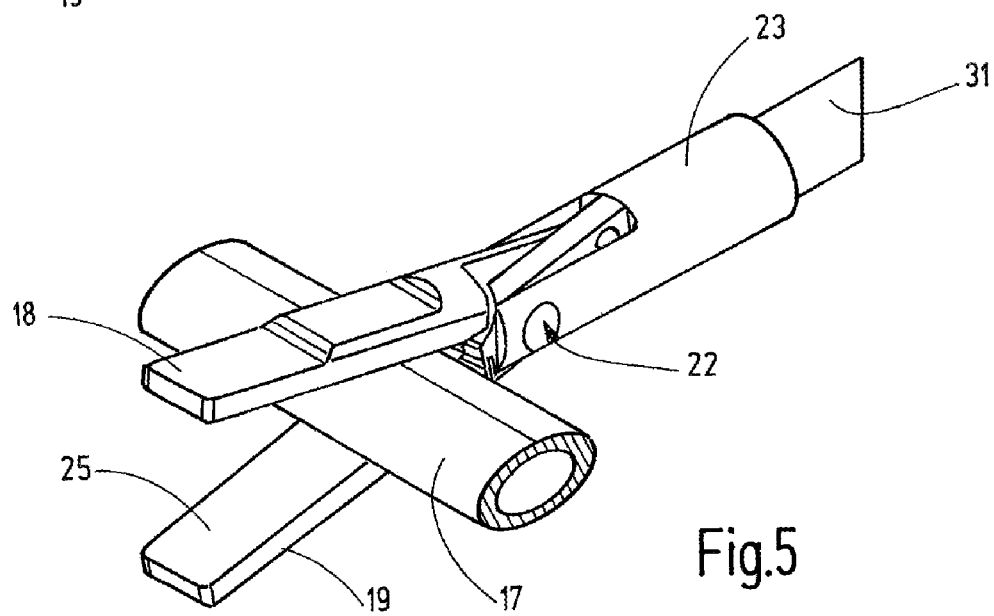

In FIG. 4 the opening angle α is half of that of FIG. 2. Consequently, the vessel 17 is partially compressed. Its previously essentially circular cross-section now becomes an oval cross-section, whose proximal part 36 is positioned closer to the hinge axis 21 than in FIG. 2. Because the reverse stroke movement of the slider element 28 is greater than the movement of part 36 of the bulging vessel, the distance D of the tissue from the abutment surface 28a is now greater than zero. In other words, there is no longer any abutment between the abutment surface 28 and the biological tissue of the vessel 17, so that the proximal spreading of the tissue is not blocked and counter-acts the hinge-proximal accumulation of tissue.

Figure 6:
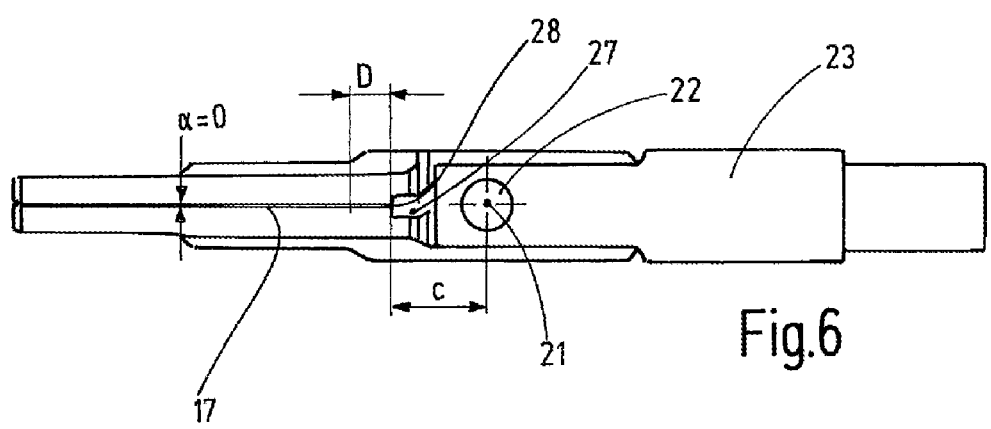
Figure 7:
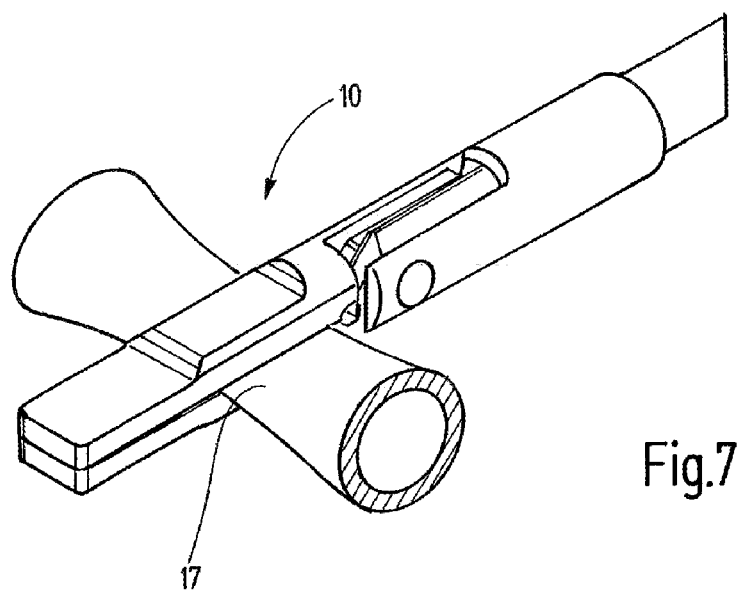

FIGS. 6 and 7 show the completely closed forceps instrument 10 (i.e., the opening angle α is equal to 0). The distance c of the tissue abutment surface 28a from the hinge axis 21 is at its minimum. The distance D of the tissue from the abutment surface 28a is at its maximum. This distance D forms a three-dimensional reserve for the expanding vessel. Consequently, conditions of a more uniform distribution over the grasping ranges can be created for vessels and tissue types that bulge or migrate more in proximal direction and would predominantly accumulate in the vicinity of the hinge, which, in turn, promotes a successful sealing of the tissue or vessels.

Figure 11:
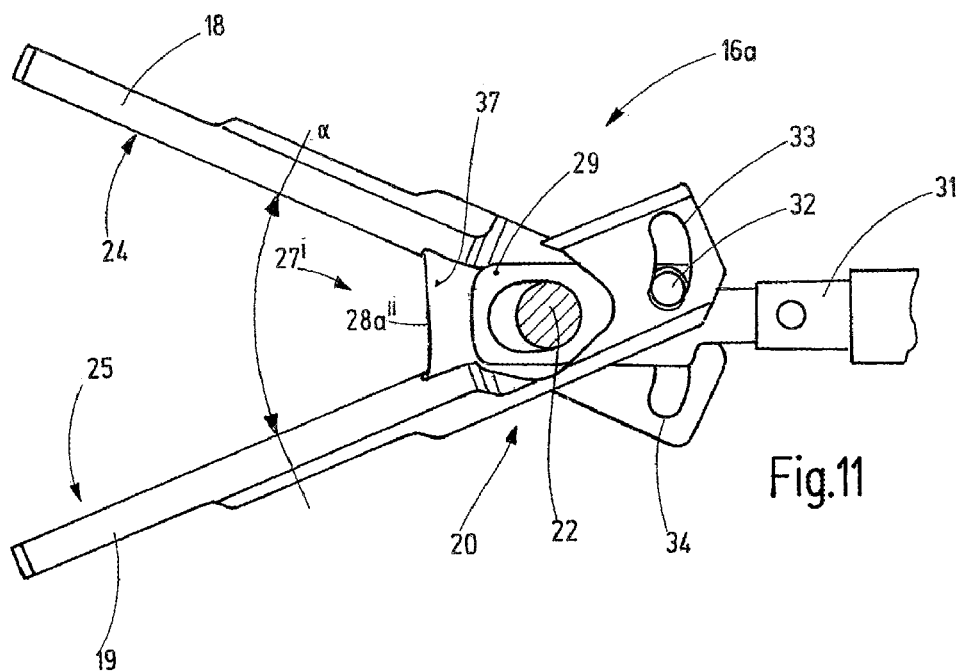
Figure 12:
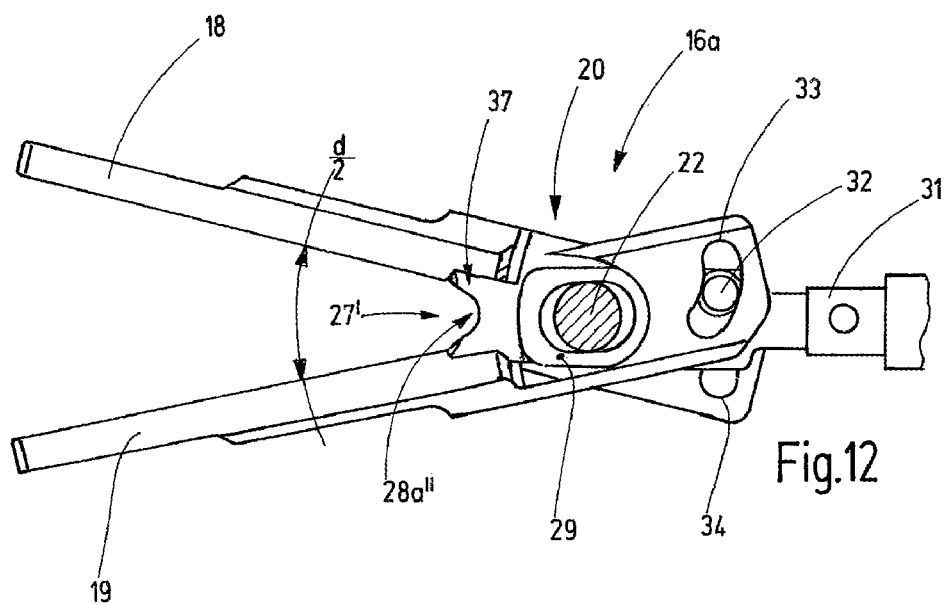

FIGS. 11 and 12 show a modified embodiment of the forceps instrument 10 with a tool 16a that corresponds to the tools described hereinabove with the exception of the description hereinbelow:

The tool 16a has a tissue abutment 27 that is configured as a spring 37, in particular a flexible spring. The spring has a section acting as the tissue abutment surface 28a", said section being displaced toward the hinge 20 when the branches 18, 19 are being closed. To do so, the spring may be configured as a flexible spring, the ends of which are supported by the two branches 18, 19. In doing so, they are supported by the branches in such a manner that the ends of the flexible spring approach each other when the branches 18, 19 are being closed.

In the case of the forceps instrument 10 according to the invention, there is preferably provided a central pull-push member that is formed, for example, by the transmission element 29 and the actuating element 31. This central push-pull member is disposed for opening and closing the branches 18, 19, as well as a variable tissue abutment 28 that is variable as a function of the degree of closure of the branches 18, 19. Preferably, the variable tissue abutment 27 is configured as a slider element 28 and can be linearly adjusted in proximal direction proportional to the opening angle α of the branches 18, 19. During the grasping operation, the vessels 17 are brought in proximal direction between the branches 18, 19. In doing so, the tissue abutment 27 acts as a spacer between the hinge region and the grasped material. When the branches 18, 19 are being closed, the vessel 17 is held stationarily and compressed. When the vessel 17 is being compressed it expands axially in distal and proximal directions. Due to a retraction of the variable tissue abutment 27 during the closing operation, room is created for the grasped material to be displaced. Consequently, tissue accumulations can be restricted and any excess stress on the tissue can be counteracted.

In another embodiment of the invention it is possible to draw conclusions—via the spatial position of the central pulling and/or pushing elements and/or via the detection of the force acting on these elements and the required pressing force, respectively—regarding the condition of the distribution of the grasped biological material, in particular the degree of accumulation in the grasping region close to the hinge and thus the tissue distribution. The detection of the path is possible, e.g., by markers that can be optically interpreted, the detection of force, e.g., by means of measuring strips and/or piezoelectric materials. The detection of the extent of the tissue distribution over the grasping region and in particular the tissue accumulation in the region close to the hinge may take place in different operating modes of the instrument. Operating modes are, in particular, the dynamic closing operating, and the stationary, closed state, during and/or after the completion of the electrosurgical use.

Based on the detected data, it is possible to implement adaptations to modes for providing the electrosurgical active effects on tissue and vessels, respectively, via the instrument. Consequently, the instrument is able to adapt, via the interpreting mode, to changing interaction conditions with tissues and vessels, respectively, whereby the latter display different mechanical qualities, in particular varying deformability, stiffness and thickness.

LIST OF REFERENCE SIGNS

10 Forceps instrument
11 Shaft
12 Proximal end of the shaft 11
13 Handle
14 Housing
15 Actuating element
16, 16a Tool
17 Vessel
18 First (upper) branch
19 Second (lower) branch
20 Hinge
21 Hinge axis
22 Hinge pin
23 Hinge bearing
24 Tissue support surface of the first branch 18
25 Tissue support surface of the second branch 19
26 Cable
27' Tissue abutment
28, 28' Slider element
28a, 28a', 28 a" Tissue abutment surface
29 transmission element
30 Slotted hole cutout
31 Actuating element
32 Follower pin
33 Slotted hole
34, 35 Rounded ends of the slider element 28, 27'
a, b, c Distance of the tissue from the hinge axis 21
D Distance of the tissue from the abutment surface 28
36 Proximal part of the vessel 17
37 Spring

The invention claimed is:

1. A medical forceps instrument (10) adapted for tissue fusion comprising:
   a tool (16) that comprises two branches (18, 19) configured to grasp and fuse biological tissue between said branches;
   a hinge (20) that supports at least one of the branches (18, 19) so as to be pivotally movable about a hinge axis (21) to allow the at least one branch to be moved toward or away from the other branch (18, 19); and
   a tissue abutment (27') that is movably arranged on the hinge (20) and has a blunt tissue abutment surface (28a, 28a', 28a") at a distal end thereof adapted for abutting the biological tissue without cutting the biological tissue;
   wherein an actuating arrangement (31) is connected to the at least one pivotally movable branch (18, 19) via a transmission arrangement (29), wherein the transmission arrangement (29) is configured such that the tissue abutment performs an escape movement in a direction toward the hinge (20) during a closing movement of the branches (18, 19).

2. The medical forceps instrument according to claim 1, wherein both branches (18, 19) are supported so as to be movable toward each other and away from each other.

3. The medical forceps instrument according to claim 1, wherein the tissue abutment (27) is supported so as to be linearly movable.

4. The medical forceps instrument according to claim 1, wherein the tissue abutment surface (28a) has a transverse dimension (b1, b2) measured in a direction parallel to the hinge axis (21), said transverse dimension being smaller than a width of one of the branches (18, 19) measured in a direction parallel to the hinge axis.

5. The medical forceps instrument according to claim 1, wherein the tissue abutment (27) is configured as a slider element (28) and the tissue abutment surface (28a) includes a projection having a width (b1, b2) measured in a direction parallel to the hinge axis (21) that is greater than a width of a remainder of the slider element (27).

6. The medical forceps instrument according to claim 1, wherein the transmission arrangement (29, 32) is a link guide.

7. The medical forceps instrument according to claim 1, wherein the two branches (18, 19) are provided with electrodes or are configured as electrodes to which an electrical voltage is applied.

\* \* \* \* \*